United States Patent
Sørensen et al.

(10) Patent No.: US 8,765,770 B2
(45) Date of Patent: Jul. 1, 2014

(54) SUBSTITUTED [1,2,4]TRIAZOLO[1,5-A]PYRIMIDINES AND THEIR USE AS POTASSIUM CHANNEL MODULATORS

(75) Inventors: Ulrik Svane Sørensen, Søborg (DK); Birgitte L. Eriksen, Farum (DK); Charlotte Hougaard, Bagsærd (DK); Dotre Strøbæk, Farum (DK); Palle Christophersen, Ballerup (DK)

(73) Assignee: Ataxion, Inc., Cambridge, MA (US)

( * ) Notice: Subject to any disclaimer, the term of this patent is extended or adjusted under 35 U.S.C. 154(b) by 61 days.

(21) Appl. No.: 13/258,923

(22) PCT Filed: Mar. 30, 2010

(86) PCT No.: PCT/EP2010/054164
§ 371 (c)(1),
(2), (4) Date: Dec. 12, 2011

(87) PCT Pub. No.: WO2010/112486
PCT Pub. Date: Oct. 7, 2010

(65) Prior Publication Data
US 2012/0088780 A1    Apr. 12, 2012

Related U.S. Application Data

(60) Provisional application No. 61/167,460, filed on Apr. 7, 2009.

(30) Foreign Application Priority Data
Apr. 1, 2009   (DK) ................................. 2009 00448

(51) Int. Cl.
  *A01N 43/90* (2006.01)
  *A61K 31/519* (2006.01)
  *C07D 487/00* (2006.01)

(52) U.S. Cl.
  USPC ..................... 514/259.31; 544/263

(58) Field of Classification Search
  None
  See application file for complete search history.

(56) References Cited

U.S. PATENT DOCUMENTS

| 5,753,665 A | 5/1998 | Sargent et al. |
| 2010/0105705 A1 | 4/2010 | Eriksen et al. |
| 2010/0120797 A1 | 5/2010 | Eriksen et al. |
| 2010/0130516 A1 | 5/2010 | Eriksen et al. |
| 2010/0152210 A1 | 6/2010 | Eriksen et al. |
| 2011/0237607 A1 | 9/2011 | Eriksen et al. |
| 2011/0251217 A1 | 10/2011 | Eriksen et al. |
| 2012/0004246 A1 | 1/2012 | Eriksen et al. |
| 2012/0095025 A1 | 4/2012 | Sorensen et al. |
| 2012/0101112 A1 | 4/2012 | Sorensen et al. |

FOREIGN PATENT DOCUMENTS

WO    WO 95/10521 A1    4/1995

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
International Search Report for PCT/EP2010/054164, mailed on Jun. 22, 2010.
A. Nardi et al., "Potassium channels as drug targets for therapeutic intervention in respiratory diseases", Expert Opinion on Therapeutic Patents, vol. 18, No. 12, 2008, XP-002585889, pp. 1361-1384.
C. Sailer et al., "Comparative immunohistochemical distribution of three small-conductance Ca2+-activated potassium channel sub-units, SK1, SK2 and SK3 in mouse brain", Molecular and Cellular Neuroscience, vol. 26, 2004, pp. 458-469.
J. -F. Liegeois et al., "Modulation of small conductance calcium-activated potassium (SK) channels: a new challenge in medicinal chemistry", Current Medicinal Chemistry, 2003, vol. 10, pp. 625-647.

* cited by examiner

*Primary Examiner* — Jeffrey H Murray
(74) *Attorney, Agent, or Firm* — Birch, Stewart, Kolasch & Birch, LLP

(57) ABSTRACT

This invention relates to novel substituted [1,2,4]triazolo[1,5-a]pyrimidines and their use as modulators of potassium channels. In other aspects the invention relates to the use of these compounds, in a method for therapy and to pharmaceutical compositions comprising the compounds of the invention.

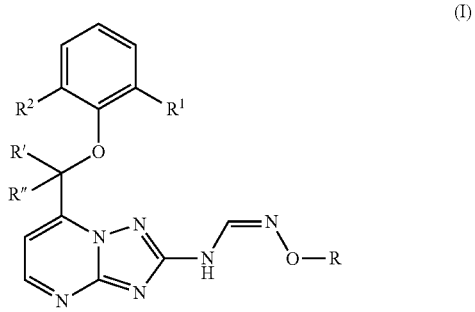

13 Claims, No Drawings

SUBSTITUTED [1,2,4]TRIAZOLO[1,5-A]PYRIMIDINES AND THEIR USE AS POTASSIUM CHANNEL MODULATORS

CROSS REFERENCE TO RELATED APPLICATIONS

This application is the National Phase of PCT/EP2010/054164 filed on Mar. 30, 2010, which claims the benefit under 35 U.S.C. 119(e) of U.S. Provisional Application No. 61/167,460 filed on Apr. 7, 2009, and claims priority under 35 U.S.C. 119 (a) to Patent Application No. PA 2009-00448 filed in Denmark on Apr. 1, 2009, all of which are hereby expressly incorporated by reference into the present application.

TECHNICAL FIELD

This invention relates to novel substituted [1,2,4]triazolo[1,5-a]pyrimidines and their use as modulators of small-conductance calcium-activated potassium channels (SK channels). Moreover the invention is directed to pharmaceutical compositions useful for the treatment or alleviation of diseases or disorders associated with the activity of potassium channels.

BACKGROUND ART

Three subtypes of small-conductance calcium-activated potassium channels (SK channels) have been cloned: SK1, SK2 and SK3 (corresponding to KCNN1-3 using the genomic nomenclature). The activity of these channels is determined by the concentration of free intracellular calcium ($[Ca^{2+}]_i$) via calmodulin that is constitutively bound to the channels. SK channels are tightly regulated by $[Ca^{2+}]_i$ in the physiological range being closed at $[Ca^{2+}]_i$ up to around 0.1 µM but fully activated at a $[Ca^{2+}]_i$ of 1 µM. Being selective for potassium, open or active SK channels have a hyperpolarizing influence on the membrane potential of the cell. SK channels are widely expressed in the central nervous system. The distribution of SK1 and SK2 show a high degree of overlap and display the highest levels of expression in neocortical, limbic and hippocampal areas in the mouse brain. In contrast, the SK3 channels show high levels of expression in the basal ganglia, thalamus and the brain stem monoaminergic neurons e.g. dorsal raphe, locus coeruleus and the ventral tegmental area (Sailer et al.: "Comparative immunohistochemical distribution of three small-conductance $Ca^{2+}$-activated potassium channel subunits, SK1, SK2 and SK3 in mouse brain", *Mol. Cell. Neurosci.* 2004 26 458-469). The SK channels are also present in several peripheral cells including skeletal muscle, gland cells, liver cells and T-lymphocytes.

The hyperpolarizing action of active SK channels plays an important role in the control of firing pattern and excitability of excitable cells. SK channel inhibitors such as apamin and quaternized anlogues of bicuculline have been demonstrated to increase excitability whereas the opener 1-EBIO is able to reduce electrical activity. In non-excitable cells where the amount of $Ca^{2+}$ influx via voltage-independent pathways is highly sensitive to the membrane potential an activation of SK channels will increase the driving force whereas a blocker of SK channels will have a depolarising effect and thus diminish the driving force for calcium.

Based on the important role of SK channels in linking $[Ca^{2+}]_i$ and membrane potential, SK channels are an interesting target for developing novel therapeutic agents.

A review of SK channels and SK channel modulators may be found in Liegeois, J.-F. et al.: "Modulation of small conductance calcium-activated potassium (SK) channels: a new challenge in medicinal chemistry", *Current Medicinal Chemistry* 2003 10 625-647.

Known modulators of SK channels suffer from being large, often positively charged, molecules or peptides (like apamin, scyllatoxin, tubocurarine, dequalinium chloride and UCL1684), or from having low potency (e.g. 1-EBIO and riluzole). Thus, there is a continued need for compounds with an optimized pharmacological profile.

The compound, N-{7-[1-(phenoxy)ethyl]-[1,2,4]triazolo[1,5-a]pyrimidin-2-yl}-N'-methoxy-formamidine; is a chemical compound which is listed at various chemical suppliers.

SUMMARY OF THE INVENTION

It is an object of the present invention to provide novel substituted [1,2,4]triazolo[1,5-a]pyrimidines capable of modulating SK channels, or subtypes of SK channels.

In one aspect, the present invention provides a compound of formula (I)

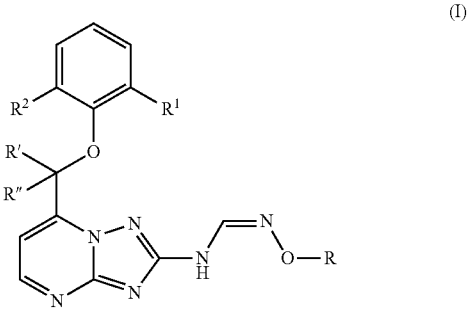

(I)

a stereoisomer or a mixture of its stereoisomers, or a pharmaceutically-acceptable addition salt thereof, or an N-oxide thereof, wherein $R^1$, $R^2$, R', R" and R are as described below.

In another aspect, the invention provides pharmaceutical compositions comprising an effective amount of a compound of the invention.

In further aspects the invention relates to the use of a compound of the invention for the manufacture of a medicament for the treatment or alleviation of diseases or disorders associated with the activity of potassium channels, and to method of treatment or alleviation of disorders or conditions responsive to modulation of potassium channels.

Another embodiment of the invention is the provision of compounds with optimal pharmacodynamic and/or pharmacokinetic properties such as kinetic behavior, bioavailability, solubility, efficacy and/or adverse effects.

Other objects of the invention will be apparent to the person skilled in the art from the following detailed description and examples.

DETAILED DISCLOSURE OF THE INVENTION

In one aspect, the present invention provides compounds of formula (I)

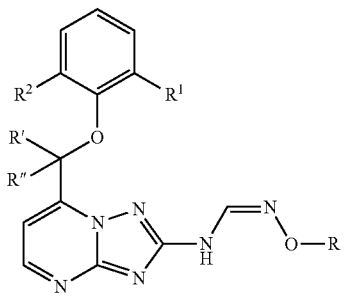

(I)

a stereoisomer or a mixture of its stereoisomers, or a pharmaceutically-acceptable addition salt thereof, or an N-oxide thereof, wherein $R^1$ and $R^2$, independently of each other, are hydrogen, halogen, $C_{1-6}$-alkyl, $C_{3-7}$-cycloalkyl or $C_{1-6}$-alkoxy;

R' and R", independently of each other, are hydrogen or $C_{1-6}$-alkyl, and R is hydrogen or $C_{1-6}$-alkyl;

with the proviso that the compound is not N-{7-[1-(Phenoxy)ethyl]-[1,2,4]triazolo[1,5-a]pyrimidin-2-yl}-N'-methoxy-formamidine.

In another embodiment of the invention, in formula (I) $R^1$ and $R^2$, independently of each other, are hydrogen, halogen, $C_{1-6}$-alkyl, $C_{3-7}$-cycloalkyl or $C_{1-6}$-alkoxy; R' and R", independently of each other, are hydrogen or $C_{1-6}$-alkyl, and R is hydrogen or $C_{1-6}$-alkyl; with the proviso that $R^1$ and $R^2$ are not both hydrogen at the same time.

In another embodiment of the invention, in formula (I) $R^1$ and $R^2$, independently of each other, are hydrogen, halogen, $C_{1-6}$-alkyl, $C_{3-7}$-cycloalkyl or $C_{1-6}$-alkoxy; R' and R", independently of each other, are hydrogen or $C_{1-6}$-alkyl, and R is hydrogen or $C_{1-6}$-alkyl; with the proviso that $R^1$, $R^2$ and R' are not all hydrogen at the same time as R" and R are both methyl.

In another embodiment of the invention, in formula (I), $R^1$ and $R^2$, independently of each other are hydrogen, halogen or $C_{1-6}$-alkyl. In another embodiment, $R^1$ and $R^2$, independently of each other are hydrogen or $C_{1-6}$-alkyl. In another embodiment $R^1$ is hydrogen. In another embodiment $R^2$ is hydrogen. In another embodiment $R^1$ is $C_{1-6}$-alkyl, e.g. methyl. In another embodiment $R^2$ is $C_{1-6}$-alkyl, e.g. methyl.

In another embodiment of the invention, in formula (I), R' and R", independently of each other, are hydrogen or $C_{1-6}$-alkyl. In another embodiment, R' and R", independently of each other, are hydrogen or $C_{2-6}$-alkyl. In another embodiment, R' and R" both are hydrogen. In another embodiment, R' and R" both are methyl.

In another embodiment of the invention, in formula (I), R is hydrogen or $C_{1-6}$-alkyl. In another embodiment of the invention, in formula (I), R is hydrogen. In another embodiment of the invention, in formula (I), R is hydrogen or $C_{1-6}$-alkyl, e.g. methyl, ethyl, propyl, isopropyl. In another embodiment of the invention, in formula (I), R is methyl.

In another embodiment of the invention, in formula (I) $R^1$ is hydrogen, halogen, $C_{1-6}$-alkyl, $C_{3-7}$-cycloalkyl or $C_{1-6}$-alkoxy; $R^2$ is halogen, $C_{1-6}$-alkyl, $C_{3-7}$-cycloalkyl or $C_{1-6}$-alkoxy; R' and R", independently of each other, are hydrogen or $C_{1-6}$-alkyl, and R is hydrogen or $C_{1-6}$-alkyl.

In another embodiment of the invention, in formula (I) $R^1$ is hydrogen; $R^2$ is $C_{1-6}$-alkyl; R' and R", independently of each other, are hydrogen or $C_{1-6}$-alkyl, and R is $C_{1-6}$-alkyl.

In another embodiment of the invention, in formula (I), $R^1$ is hydrogen; $R^2$ is $C_{1-6}$-alkyl; R' and R", independently of each other, are hydrogen or $C_{1-6}$-alkyl, and R is hydrogen.

In another embodiment of the invention, in formula (I), $R^1$ and $R^2$, independently of each other, are hydrogen, halogen, $C_{1-6}$-alkyl, $C_{3-7}$-cycloalkyl or $C_{1-6}$-alkoxy; R' and R", independently of each other, are hydrogen or $C_{1-6}$-alkyl, and R is hydrogen or $C_{2-6}$-alkyl.

In another embodiment of the invention, in formula (I), $R^1$ and $R^2$, independently of each other, are hydrogen, halogen, $C_{1-6}$-alkyl, $C_{3-7}$-cycloalkyl or $C_{1-6}$-alkoxy; R' and R", independently of each other, are hydrogen or $C_{2-6}$-alkyl, or R' and R" both are hydrogen; or R' and R" both are methyl; and R is hydrogen or $C_{1-6}$-alkyl.

In another embodiment of the invention, the compound of the invention is: N-{7-[1-(2-Methylphenoxy)ethyl]-[1,2,4]triazolo[1,5-a]pyrimidin-2-yl}-N'-methoxy-formamidine; or a stereoisomer or a mixture of its stereoisomers, or a pharmaceutically-acceptable addition salt thereof, or an N-oxide thereof.

In another embodiment, the invention relates to a pharmaceutical composition comprising a therapeutically effective amount of the compound of the formula (I)

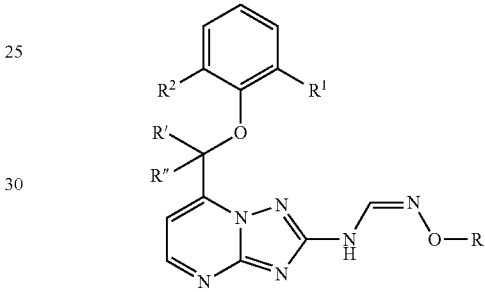

(I)

a stereoisomer or a mixture of its stereoisomers, or a pharmaceutically-acceptable addition salt thereof, or an N-oxide thereof, wherein $R^1$ and $R^2$, independently of each other, are hydrogen, halogen, $C_{1-6}$-alkyl, $C_{3-7}$-cycloalkyl or $C_{1-6}$-alkoxy;

R' and R", independently of each other, are hydrogen or $C_{1-6}$-alkyl, and

R is hydrogen or $C_{1-6}$-alkyl.

In another embodiment of the invention, in the pharmaceutical composition, in formula (I), $R^1$ and $R^2$, independently of each other, are hydrogen or $C_{1-6}$-alkyl; R' and R", independently of each other, are hydrogen or $C_{1-6}$-alkyl, and R is hydrogen or $C_{1-6}$-alkyl.

In another embodiment, in the pharmaceutical composition, in formula (I), $R^1$ and $R^2$, independently of each other, are hydrogen or $C_{1-6}$-alkyl; R' is hydrogen; R" is $C_{1-6}$-alkyl, and R is $C_{1-6}$-alkyl.

In another embodiment, in the pharmaceutical composition, in formula (I), $R^1$ and $R^2$ are hydrogen; R' is hydrogen; R" is $C_{1-6}$-alkyl, and R is $C_{1-3}$-alkyl.

In another embodiment, in the pharmaceutical composition, in formula (I), $R^1$ is hydrogen; $R^2$ is $C_{1-6}$-alkyl; R' is hydrogen; R" is methyl, and R is $C_{1-3}$-alkyl.

In another embodiment of the invention, in the pharmaceutical composition, the compound is:

N-{7-[1-(Phenoxy)ethyl]-[1,2,4]triazolo[1,5-a]pyrimidin-2-yl}-N'-methoxy-formamidine;

N-{7-[1-(2-Methylphenoxy)ethyl]-[1,2,4]triazolo[1,5-a]pyrimidin-2-yl}-N'-methoxy-formamidine;

or a stereoisomer or a mixture of its stereoisomers, or a pharmaceutically-acceptable addition salt thereof, or an N-oxide thereof.

In another embodiment, the invention relates to the use of the compound of formula (I)

(I)

a stereoisomer or a mixture of its stereoisomers, or a pharmaceutically-acceptable addition salt thereof, or an N-oxide thereof, wherein $R^1$ and $R^2$, independently of each other, are hydrogen, halogen, $C_{1-6}$-alkyl, $C_{3-7}$-cycloalkyl or $C_{1-6}$-alkoxy;

R' and R", independently of each other, are hydrogen or $C_{1-6}$-alkyl, and

R is hydrogen or $C_{1-6}$-alkyl, for the manufacture of a pharmaceutical composition.

In another embodiment, the invention relates to the use of the compound of formula (I) wherein $R^1$ and $R^2$, independently of each other, are hydrogen, halogen, $C_{1-6}$-alkyl, $C_{3-7}$-cycloalkyl or $C_{1-6}$-alkoxy;

R' and R", independently of each other, are hydrogen or $C_{1-6}$-alkyl, and

R is hydrogen or $C_{1-6}$-alkyl, for the manufacture of a pharmaceutical composition for the treatment, prevention or alleviation of a disease or a disorder or a condition of a mammal, including a human, which disease, disorder or condition is responsive to modulation of SK channels.

In another embodiment the compound for use according to the invention is of formula (I), wherein $R^1$ and $R^2$, independently of each other, are hydrogen or $C_{1-6}$-alkyl; R' and R", independently of each other, are hydrogen or $C_{1-6}$-alkyl, and R is hydrogen or $C_{1-6}$-alkyl.

In another embodiment the compound for use according to the invention is of formula (I), wherein $R^1$ and $R^2$, independently of each other, are hydrogen or $C_{1-6}$-alkyl; R' is hydrogen; R" is $C_{1-6}$-alkyl, and R is $C_{1-6}$-alkyl.

In another embodiment the compound for use according to the invention is of formula (I), wherein $R^1$ and $R^2$ are hydrogen; R' is hydrogen; R" is $C_{1-6}$-alkyl, and R is $C_{1-3}$-alkyl.

In another embodiment the compound for use according to the invention is of formula (I), wherein one of $R^1$ and $R^2$ is hydrogen, and the other one of $R^1$ and $R^2$ is $C_{1-6}$-alkyl; R' is hydrogen R" is methyl, and R is $C_{1-3}$-alkyl.

In another embodiment the compound for use according to the invention is:

N-{7-[1-(Phenoxy)ethyl]-[1,2,4]triazolo[1,5-a]pyrimidin-2-yl}-N'-methoxy-formamidine;

N-{7-[1-(2-Methylphenoxy)ethyl]-[1,2,4]triazolo[1,5-a]pyrimidin-2-yl}-N'-methoxy-formamidine;

or a stereoisomer or a mixture of its stereoisomers, or a pharmaceutically-acceptable addition salt thereof, or an N-oxide thereof.

Any combination of two or more of the embodiments described herein is considered within the scope of the present invention.

Definition Of Terms as used throughout the present specification and appended claims, the following terms have the indicated meaning:

The term "$C_{1-6}$-alkyl" as used herein means a saturated, branched or straight hydrocarbon group having from 1-6 carbon atoms, e.g. $C_{1-3}$-alkyl, $C_{1-4}$-alkyl, $C_{1-5}$-alkyl, $C_{2-6}$-alkyl, $C_{3-6}$-alkyl, and the like. Representative examples are methyl, ethyl, propyl (e.g. prop-1-yl, prop-2-yl (or iso-propyl)), butyl (e.g. 2-methylprop-2-yl (or tert-butyl), but-1-yl, but-2-yl), pentyl (e.g. pent-1-yl, pent-2-yl, pent-3-yl), 2-methylbut-1-yl, 3-methylbut-1-yl, hexyl (e.g. hex-1-yl), and the like.

The term "halo" or "halogen" means fluorine, chlorine, bromine or iodine.

The term "hydroxy" shall mean the radical —OH.

The term "$C_{1-6}$-alkoxy" as used herein refers to the radical —O—$C_{1-6}$-alkyl.

Representative examples are methoxy, ethoxy, propoxy (e.g. 1-propoxy, 2-propoxy), butoxy (e.g. 1-butoxy, 2-butoxy, 2-methyl-2-propoxy), pentoxy (1-pentoxy, 2-pentoxy), hexoxy (1-hexoxy, 3-hexoxy), and the like.

The term "$C_{3-7}$-cycloalkyl" as used herein refers to a saturated monocyclic carbocyclic ring having from 3 to 7 carbon atoms, e.g. $C_{3-4}$-alkyl, $C_{3-5}$-alkyl, $C_{3-6}$-alkyl, $C_{4-7}$-alkyl, $C_{4-6}$-alkyl, $C_{5-7}$-alkyl and the like. Representative examples are cyclopropyl, cyclobutyl, cyclopentyl, cyclohexyl, cycloheptyl, and the like.

The term "optionally substituted" as used herein means that the groups in question are either unsubstituted or substituted with one or more of the substituents specified. When the group(s) in question is/are substituted with more than one substituent the substituents may be the same or different.

Certain of the defined terms may occur more than once in the structural formulae, and upon such occurrence each term shall be defined independently of the other.

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

The terms "disease", "condition" and "disorder" as used herein are used interchangeably to specify a state of a patient which is not the normal physiological state of man.

The term "medicament" as used herein means a pharmaceutical composition suitable for administration of the pharmaceutically active compound to a patient.

The term "pharmaceutically acceptable" as used herein means suited for normal pharmaceutical applications, i.e. giving rise to no adverse events in patients etc.

The term "effective amount" as used herein means a dosage which is sufficient in order for the treatment of the patient to be effective compared with no treatment.

The term "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

Steric Isomers

It will be appreciated by those skilled in the art that the compounds of the present invention may exist in different stereoisomeric forms—including enantiomers, diastereomers and cis-trans-isomers.

The invention includes all such stereoisomers and any mixtures thereof including racemic mixtures.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in *Enantiomers, Racemates, and Resolutions*, John Wiley and Sons, New York (1981).

Moreover, some of the chemical compounds of the invention being oximes, may thus exist in two forms, syn- and anti-form (Z- and E-form), depending on the arrangement of the substituents around the —C=N— double bond. A chemical compound of the present invention may thus be the syn- or the anti-form (Z- and E-form), or it may be a mixture hereof.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention, including compounds modified at one or more reactive or derivatizable groups of the parent compound. Of particular interest are compounds modified at a carboxyl group, a hydroxyl group, or an amino group. Examples of suitable derivatives are esters or amides.

The compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Methods of Preparation

The compounds of the invention may be prepared by conventional methods of chemical synthesis, e.g. those described in the working examples. The starting materials for the processes described in the present application are known or may readily be prepared by conventional methods from commercially available chemicals.

The end products of the reactions described herein may be isolated by conventional techniques, e.g. by extraction, crystallisation, distillation, chromatography, etc.

Biological Activity

The compounds of the invention may be tested for their usefulness as potassium channel modulating agents e.g. such as described in WO2006/100212.

The compounds of the invention may be tested for their ability to modulate SK channels in vitro. Functional modulation can be determined by measuring the compound-induced change in SK current by the patch clamp technique as described in Strøbæk et al.: "Pharmacological characterization of small-conductance $Ca^{2+}$-activated K channels expressed in HEK293 cells", British Journal of Pharmacology (2000) 129, 991-999. From this type of measurements the potency of a given compound can be determined as e.g. $K_i$ or $IC_{50}$ values for blockers/inhibitors and $EC_{50}$ values for openers/activators. Similar data can be obtained from other patch clamp configurations and from channels expressed endogenously in various cell lines.

The compounds of the invention are capable of selectively modulating SK1, SK2 and/or SK3 channels. Therefore, in another aspect, the invention relates to the use of the compounds of the invention for the manufacture of medicaments, which medicament may be useful for the treatment or alleviation of a disease or a disorder associated with the activity of potassium channels, e.g. SK channels, e.g. SK1, SK2 and/or SK3 channels.

In one embodiment, the compounds of the invention show selectivity for SK3 over SK1 and SK2. In another embodiment, the compounds of the invention show selectivity for SK1 over SK2 and SK3. In another embodiment, the compounds of the invention show selectivity for SK2 over SK1 and SK3. In another embodiment, the compounds of the invention are positive SK channel modulators, such as positive SK3 channel modulators. In another embodiment, the compounds of the invention are negative modulators, such as negative SK3 channel modulators. In another embodiment, the compounds of the invention are SK channel blockers, such as SK3 channel blockers.

In another embodiment, the compound of the invention is considered useful for the treatment, prevention or alleviation of a disease or a disorder or a condition responsive to modulation of SK channels.

In another embodiment, the compounds of the invention are considered useful for the treatment, prevention or alleviation of absence seizures, of absence seizures, agerelated memory loss, addiction, Alzheimer's disease, angina pectoris, arrhythmia, asthma, anxiety, ataxia, attention deficits, baldness, bipolar disorder, bladder hyperexcitability, bladder outflow obstruction, bladder spasms, brain tumours, cancer, cardiovascular disorders, cerebral ischaemia, chronic obstructive pulmonary disease (COPD), cognitive dysfunction, colitis, constipation, convulsions, coronary artery spasms, coronary heart disease, cystic fibrosis, dementia, depression, diabetes type II, dyskinesia, dysmenorrhoea, eating disorder, epilepsy, erectile dysfunction, gastrointestinal dysfunction, gastroesophageal reflux disorder, gastrointestinal hypomotility disorders, gastrointestinal motility insufficiency, hair loss, hearing loss, hyperinsulinemia, hypertension, immune suppression, inflammatory bowel disease, inflammatory pain, intermittent claudication, interstitial cystitis (IC), irritable bowel syndrome, ischaemia, ischaemic heart disease, learning deficiencies, mania, manic depression, memory and attention deficits, migraine, mood disorders, motor neuron diseases, myokymia, myotonic dystrophy, myotonic muscle dystrophia, narcolepsy, neuropathic pain, overactive bladder (OAB), pain, Parkinson's disease, polycystic kidney disease, postoperative ileus, premature labour, psychosis, psychotic disorders, renal disorders, Reynaud's disease, rhinorrhoea, secretory diarrhoea, seizures, Sjogren's syndrome, sleep disorders, sleep apnea, spasticity, stroke, traumatic brain injury, trigeminal neuralgia, urinary incontinence, urinogenital disorders, vascular spasms, vision loss, and xerostomia.

In another embodiment the compounds of the invention are considered useful for the treatment, prevention or alleviation of parkinsonism, dementia of ageing, senile dementia, acquired immunodeficiency syndrome dementia complex, memory dysfunction in ageing, pseudodementia, memory loss, attention deficit hyperactivity disorder, chronic fatigue syndrome, premenstrual syndrome, late luteal phase syndrome, post-traumatic syndrome, obesity, eating disorder, bulimia, anorexia nervosa, binge eating disorder (BED), premature ejaculation, erectile difficulty, social phobia, panic disorder, autism, trichotillomania, mutism, akinetic mutism, hysterical mutism, selective mutism, hearing mutism, Gilles de la Tourettes disease, Ganser's syndrome, narcolepsy, addiction, e.g. drug addiction, drug misuse, cocaine abuse, nicotine abuse, tobacco abuse, alcohol addiction or alcoholism, or withdrawal symptoms caused by termination of abuse of chemical substances, e.g. opioids, heroin, cocaine and morphine, and alcohol.

In another embodiment, the compounds of the invention are considered useful for the treatment, prevention or alleviation of a respiratory disease, urinary incontinence, erectile dysfunction, anxiety, epilepsy, psychosis, schizophrenia, bipolar disorder, depression, amyotrophic lateral sclerosis (ALS), Parkinson's disease or pain.

In another embodiment, the compounds of the invention are considered useful for the treatment, prevention or alleviation of psychosis, schizophrenia, bipolar disorder, depression, epilepsy, Parkinson's disease or pain.

In another embodiment, the compounds of the invention are considered useful for the treatment, prevention or alleviation of pain, mild or moderate or severe pain, pain of acute, chronic or recurrent character, pelvic pain or abdominal pain, pain caused by migraine, postoperative pain, phantom limb pain, inflammatory pain, neuropathic pain, chronic headache, central pain, pain related to diabetic neuropathy, to post therapeutic neuralgia, or to peripheral nerve injury.

In another embodiment, the compounds of the invention are considered useful for the treatment, prevention or alleviation of depression. In another embodiment, the compounds of the invention are considered useful for the treatment, prevention or alleviation of cardiovascular disorders. In another embodiment, the compounds of the invention are considered useful for the treatment, prevention or alleviation of cognitive dysfunction. In another embodiment, the compounds of the invention are considered useful for the treatment, prevention or alleviation of diabetes type II. In another embodiment, the compounds of the invention are considered useful for the treatment, prevention or alleviation of gastrointestinal dysfunction. In another embodiment, the compounds of the invention are considered useful for the treatment, prevention or alleviation of hypertension. In another embodiment, the compounds of the invention are considered useful for the treatment, prevention or alleviation of hypertension of overactive bladder (OAB). In another embodiment, the compounds of the invention are considered useful for the treatment, prevention or alleviation of pain. In another embodiment, the compounds of the invention are considered useful for the treatment, prevention or alleviation of Parkinson's disease. In another embodiment, the compounds of the invention are considered useful for the treatment, prevention or alleviation of urinary incontinence. In another embodiment, the compounds of the invention are considered useful for the treatment, prevention or alleviation of ataxia. In another embodiment, the compounds of the invention are considered useful for the treatment, prevention or alleviation of amyotrophic lateral sclerosis (ALS).

The compounds tested showed a biological activity determined as described herein in the micromolar and sub-micromolar range, i.e. of from below 1 to above 100 µM e.g. from below 0.1 to about 10 µM.

Pharmaceutical Compositions

In yet another aspect the invention provides novel pharmaceutical compositions comprising a therapeutically effective amount of the compounds of the invention.

While a compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers and/or diluents.

In another embodiment, the invention provides pharmaceutical compositions comprising the compound of the invention, or a pharmaceutically acceptable salt or compound thereof, together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Pharmaceutical compositions of the invention may be those suitable for oral, rectal, bronchial, nasal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The compounds of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

For topical administration to the epidermis the chemical compound according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

In one embodiment, the invention provides tablets or capsules for oral administration In another embodiment, the invention provides and liquids for intravenous administration and continuous infusion.

Further details on techniques for formulation and administration may be found in the latest edition of *Remington's Pharmaceutical Sciences* (Maack Publishing Co., Easton, Pa.).

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated and the route of administration, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, e.g. from about 1 to about 100 mg, e.g. from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Other ranges are from about 0.1 µg/kg to about 10 mg/kg/day i.v., and from about 1 µg/kg to about 100 mg/kg/day p.o.

Methods of Therapy

In another aspect the invention provides a method for the prevention, treatment or alleviation of a disease or a disorder or a condition of a living animal body, including a human, which disease, disorder or condition is responsive to modulation of potassium channels, in particular SK channels, and which method comprises comprising administering to such a living animal body, including a human, in need thereof a therapeutically-effective amount of a compound of the invention.

The indications contemplated according to the invention are those stated above.

It is at present contemplated that suitable dosage ranges are 0.1 to 1000 milligrams daily, 10-500 milligrams daily, or 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Other ranges are from about 0.001 to about 1 mg/kg i.v. and from about 0.1 to about 10 mg/kg p.o.

EXAMPLES

The following examples refer to intermediate compounds and final products for general formula (I) identified in the specification. The preparation of the compounds of general formula (I) of the present invention is described in detail using the following examples. Occasionally, the reaction may not be applicable as described to each compound included within the disclosed scope of the invention.

The compounds for which this occurs will be readily recognized by those skilled in the art. In these cases the reactions can be successfully performed by conventional modifications known to those skilled in the art, which is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials.

The abbreviations as used in the examples have the following meaning:
Ac: acetyl
Et: ethyl
Me: methyl
EtOAc: Ethyl acetate
rt: room temperature
Procedure A
Step A: A substituted phenol derivative and 3-chloro-2-butanone, or alternatively another alpha-halogenated keto derivative, were dissolved in acetonitrile and potassium carbonate was added. The reaction mixture was refluxed until complete conversion of the phenol. The mixture was then cooled to rt, filtered, evaporated under reduced pressure and the remaining oil was then dissolved in dichloromethane and washed with aqueous sodium carbonate and water. The organic layer was dried, the solvent removed under reduced pressure and the desired intermediate could be purified by distillation or by column chromatography.
Step B: The isolated intermediate from Step A and dimethyl formamide dimethyl acetal (1.2 eq) were heated at 120° C. with removal of the formed methanol. After complete reaction, the mixture was cooled to rt and the remaining crude product was purified by column chromatography (EtOAc/hexane) or used without further purification in the subsequent reaction step.
Step C: The intermediate from Step B and diamino-1,2,4-triazole (1 eq) were dissolved in acetic acid and heated to reflux for 30-60 min. The reaction mixture was allowed to cool to rt, triturated with diethyl ether and the desired product isolated by filtration. This crude product could be purified by column chromatography (dichloromethane/methanol) or used in the next step without further purification.

Step D: The [1,2,4]triazolo[1,5-a]pyrimidin-2-ylamine derivative formed in Step C was dissolved in acetonitrile and added dimethyl formamide dimethyl acetal (1.2 eq) and the reaction mixture was refluxed 1 h and allowed to cool to rt. The desired product could be isolated as a solid by filtration or by removal of the solvent under reduced pressure. The crude product was used without further purification in Step E.

Step E: The N,N-dimethyl-N'-[1,2,4]triazolo[1,5-a]pyrimidin-2-yl-formamidine derivative from Step D and the required hydroxylamine derivative (1 eq) were dissolved in methanol, heated to reflux and cooled to rt. The desired product was isolated as a solid after filtration and washing with methanol or by purification using column chromatography.

An example of Procedure A, the preparation of N-{7-[1-(2-methylphenoxy)-ethyl]-[1,2,4]triazolo[1,5-a]pyrimidin-2-yl}-N'-methoxy-formamidine, is shown in Scheme 1.

Scheme 1

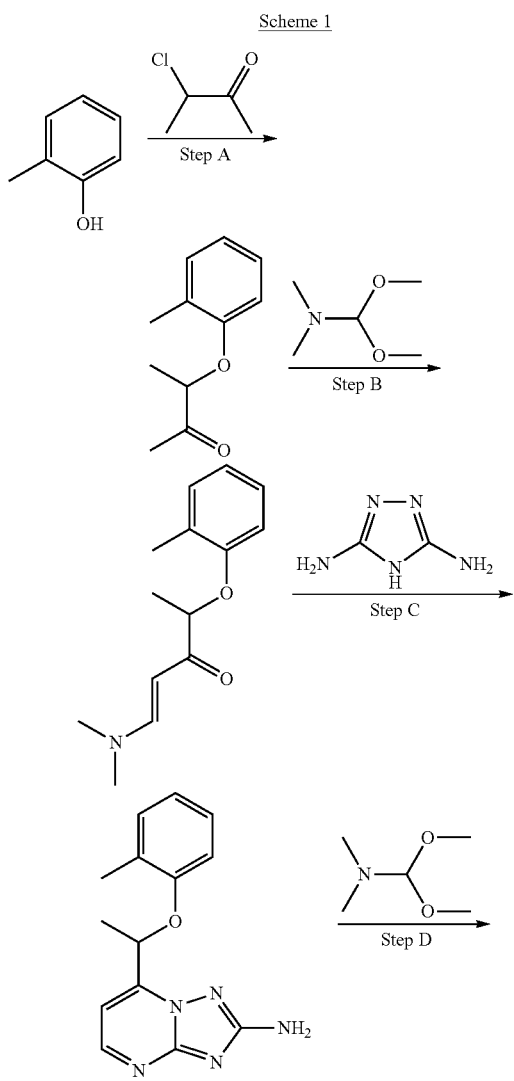

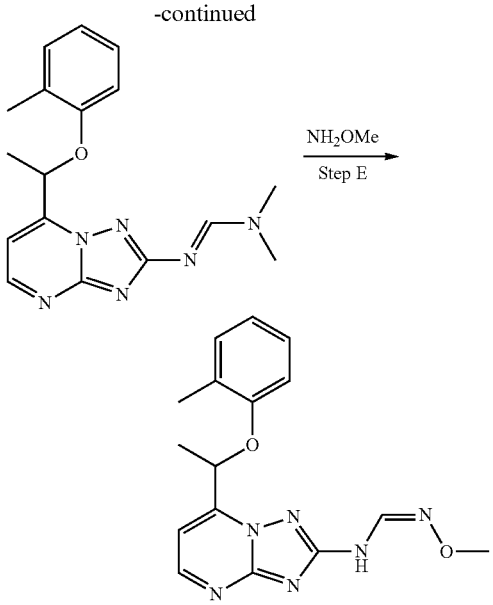

Example A

N-{7-[1-(Phenoxy)ethyl]-[1,2,4]triazolo[1,5-a]pyrimidin-2-yl}-N'-methoxy-formamidine The title compound, listed at various chemical suppliers, is prepared as described in Procedure A.

Example 1

N-{7-[1-(2-Methylphenoxy)ethyl]-[1,2,4]triazolo[1,5-a]pyrimidin-2-yl}-N'-methoxy-formamidine The title compound was prepared as described in Procedure A (starting from 2-methyl-phenol and 3-chloro-2-butanone) and isolated by filtration to give the title compound as the parent compound.

HR-MS: 327.1569 ([M+1]$^+$, $C_{16}H_{19}N_6O_2$; calc. 327.156949).

Example 2

Biological Activity

This example demonstrates the biological activity of the compounds of the invention. The ionic current through small-conductance $Ca^{2+}$-activated $K^+$ channels (SK channels, subtype 1) is recorded using the whole-cell configuration of the patch-clamp technique in a classic patch-clamp set-up using HEK293 tissue culture cells expressing hSK1 channels as described in e.g. WO 2006/100212.

The $SC_{100}$ value determined is defined as the Stimulating Concentration required for increasing the baseline current by 100%. The below $SC_{100}$ values are an indication of the SK1 activating properties of the compounds of the invention.

| Example | $SC_{100}$ (μM) |
| --- | --- |
| A | 0.20 |
| 1 | 0.02 |

The invention claimed is:

1. A compound of the formula (I)

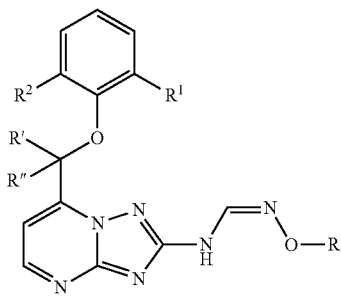

a stereoisomer or a mixture of its stereoisomers, or a pharmaceutically acceptable addition salt thereof, wherein $R^1$ and $R^2$, independently of each other, are hydrogen, halogen, $C_{1-6}$-alkyl, $C_{3-7}$-cycloalkyl or $C_{1-6}$-alkoxy;

R' and R", independently of each other, are hydrogen or $C_{1-6}$-alkyl, and

R is hydrogen or $C_{1-6}$-alkyl;

with the proviso that the compound is not N-{7-[1-(Phenoxy)ethyl]-[1,2,4]triazolo[1,5-a]pyrimidin-2-yl}-N'-methoxy-formamidine.

2. A compound of the formula (I)

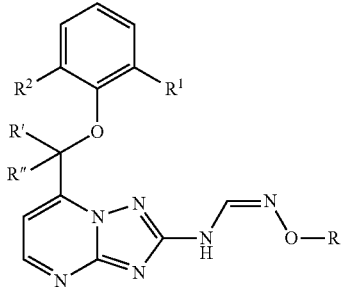

a stereoisomer or a mixture of its stereoisomers, or a pharmaceutically acceptable addition salt thereof, wherein $R^1$ is hydrogen, halogen, $C_{1-6}$-alkyl, $C_{3-7}$-cycloalkyl or $C_{1-6}$-alkoxy, $R^2$ is halogen, $C_{1-6}$-alkyl, $C_{3-7}$-cycloalkyl or $C_{1-6}$-alkoxy;

R' and R", independently of each other, are hydrogen or $C_{1-6}$-alkyl, and R is hydrogen or $C_{1-6}$-alkyl.

3. A compound of the formula (I),

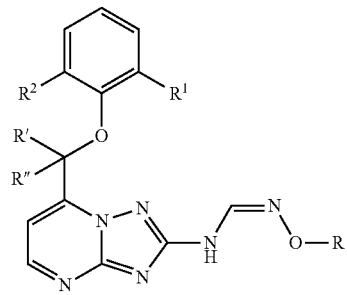

a stereoisomer or a mixture of its stereoisomers, or a pharmaceutically acceptable addition salt thereof, wherein $R^1$ and $R^2$, independently of each other, are hydrogen, halogen, $C_{1-6}$-alkyl, $C_{3-7}$-cycloalkyl or $C_{1-6}$-alkoxy;

R' and R", independently of each other, are hydrogen or $C_{1-6}$-alkyl, and

R is hydrogen or $C_{2-6}$-alkyl.

4. A compound of the formula (I)

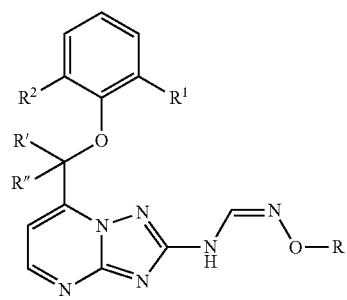

a stereoisomer or a mixture of its stereoisomers, or a pharmaceutically acceptable addition salt thereof, wherein $R^1$ and $R^2$, independently of each other, are hydrogen, halogen, $C_{1-6}$-alkyl, $C_{3-7}$-cycloalkyl or $C_{1-6}$-alkoxy;

R' and R", independently of each other, are hydrogen or $C_{2-6}$-alkyl, or R' and R" both are hydrogen; or R' and R" both are methyl; and R is hydrogen or $C_{1-6}$-alkyl.

5. The compound according to claim 1, which is:
N-{7-[1-(2-Methylphenoxy)ethyl]-[1,2,4]triazolo[1,5-a]pyrimidin-2-yl}-N'-methoxy-formamidine;
or a stereoisomer or a mixture of its stereoisomers, or a pharmaceutically acceptable addition salt thereof.

6. A pharmaceutical composition comprising a therapeutically effective amount of the compound of the formula (I)

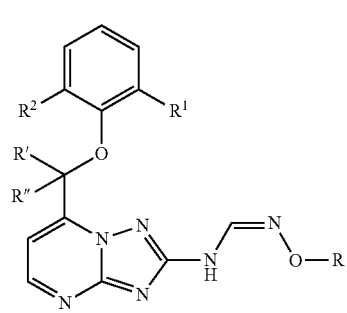

a stereoisomer or a mixture of its stereoisomers, or a pharmaceutically acceptable addition salt thereof, wherein $R^1$ and $R^2$, independently of each other, are hydrogen, halogen, $C_{1-6}$-alkyl, $C_{3-7}$-cycloalkyl or $C_{1-6}$-alkoxy;

R' and R", independently of each other, are hydrogen or $C_{1-6}$-alkyl, and

R is hydrogen or $C_{1-6}$-alkyl.

7. The pharmaceutical composition according to claim 6, wherein the compound is:

N-{7-[1-(Phenoxy)ethyl]-[1,2,4]triazolo[1,5-a]pyrimidin-2-yl}-N'-methoxy-formamidine; or N-{7-[1-(2-Methylphenoxy)ethyl]-[1,2,4]triazolo[1,5-a]pyrimidin-2-yl}-N'-methoxy-formamidine;

or a stereoisomer or a mixture of its stereoisomers, or a pharmaceutically acceptable addition salt thereof.

8. A method of modulation of SK channels, which method comprises the step of contacting a cell with a compound of the formula (I)

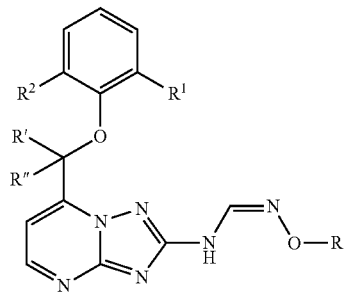

a stereoisomer or a mixture of its stereoisomers, or a pharmaceutically acceptable addition salt thereof, wherein $R^1$ and $R^2$, independently of each other, are hydrogen, halogen, $C_{1-6}$-alkyl, $C_{3-7}$-cycloalkyl or $C_{1-6}$-alkoxy;

R' and R", independently of each other, are hydrogen or $C_{1-6}$-alkyl, and

R is hydrogen or $C_{1-6}$-alkyl.

9. The method according to claim 8, wherein the compound is:

N-{7-[1-(Phenoxy)ethyl]-[1,2,4]triazolo[1,5-a]pyrimidin-2-yl}-N'-methoxy-formamidine, or N-{7-[1-(2-Methylphenoxy)ethyl]-[1,2,4]triazolo[1,5-a]pyrimidin-2-yl}-N'-methoxy-formamidine;

or a stereoisomer or a mixture of its stereoisomers, or a pharmaceutically acceptable addition salt thereof.

10. The method according to claim 8, wherein the cell is contacted with the compound, its stereoisomer or a mixture of its stereoisomers, or a pharmaceutically acceptable addition salt thereof, in vitro.

11. A method of treatment or alleviation of a disease or a disorder or a condition of a human, which method comprises the step of administering to said human in need thereof, a therapeutically effective amount of the compound of claim 6, wherein the disease or disorder is psychosis, schizophrenia, bipolar disorder, depression, epilepsy, Parkinson's disease or pain.

12. A method of treatment or alleviation of a disease or a disorder or a condition of a human, which method comprises the step of administering to said human in need thereof, a therapeutically effective amount of the compound of claim 6, wherein the disease or disorder is epilepsy, seizures, stroke or traumatic brain injury.

13. A method of treatment or alleviation of a disease or a disorder or a condition of a human, which method comprises the step of administering to said human in need thereof, a therapeutically effective amount of the compound of claim 6, wherein the disease or disorder is angina pectoris, arrhythmia, asthma or chronic obstructive pulmonary disease.

* * * * *